United States Patent [19]
Rosenwald

[11] Patent Number: 5,395,399
[45] Date of Patent: Mar. 7, 1995

[54] THERMAL WRAP FOR A BODY MEMBER

[75] Inventor: Mark A. Rosenwald, Copper Mountain, Colo.

[73] Assignee: Sport Wrapz, Inc., Chicago, Ill.

[21] Appl. No.: 76,157

[22] Filed: Jun. 14, 1993

[51] Int. Cl.$^6$ .............................................. A61F 7/00
[52] U.S. Cl. .................................. 107/108; 607/111; 607/112; 607/114
[58] Field of Search ............... 607/108, 109, 111, 112, 607/114, 110; 383/901; 62/530

[56] References Cited

U.S. PATENT DOCUMENTS

| | | |
|---|---|---|
| 2,949,914 | 8/1960 | Waldrum . |
| 4,527,566 | 7/1985 | Abare ................................. 607/112 |
| 4,628,932 | 12/1986 | Tampa . |
| 4,641,655 | 2/1987 | Abt . |
| 4,688,572 | 8/1987 | Hubbard et al. . |
| 4,776,042 | 10/1988 | Hanson et al. . |
| 4,805,619 | 2/1989 | Swearingen . |
| 4,899,749 | 2/1990 | Laroco . |
| 4,972,832 | 11/1990 | Trapini et al. ....................... 607/108 |
| 4,976,262 | 12/1990 | Palmacci . |
| 5,026,711 | 6/1991 | Kelley ................................. 607/114 |
| 5,062,414 | 11/1991 | Grim ................................... 607/108 |
| 5,074,300 | 12/1992 | Murphy . |
| 5,148,804 | 9/1992 | Hill et al. ............................ 607/108 |

Primary Examiner—Lee S. Cohen
Assistant Examiner—Robert L. Nasser, Jr.
Attorney, Agent, or Firm—Reising, Ethington, Barnard, Perry & Milton

[57] ABSTRACT

A thermal wrap is disclosed for application to body members, especially joints and limbs. It comprises a pouch for containing a thermal medium and which is constructed of a flexible elastic cloth. The pouch is mounted on a support member, also constructed of a flexible elastic cloth, which is adapted to wrap around a limb or joint. The support member is provided with a wrap fastener such as a hook and loop fastener which is adjustable to establish the desired degree of compression on the affected area. The wrap is provided with cinch bands which encircle the limb at locations above and below the pouch. This arrangement provides compression under the bandwidth of the pouch which is independently adjustable relative to the compression under the cinch bands. Additionally, a pressurized air bladder may be provided to independently adjust the compression under the bandwidth of the bladder.

19 Claims, 5 Drawing Sheets

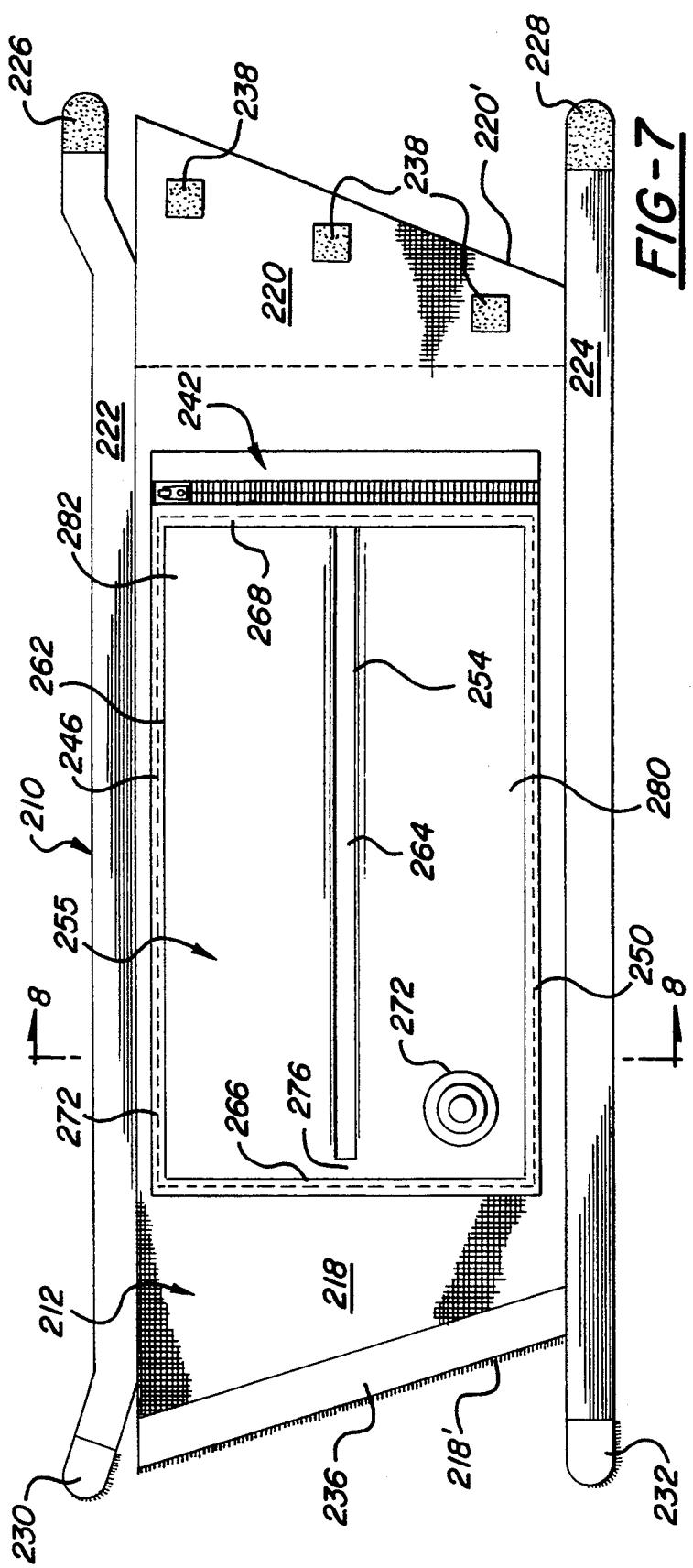
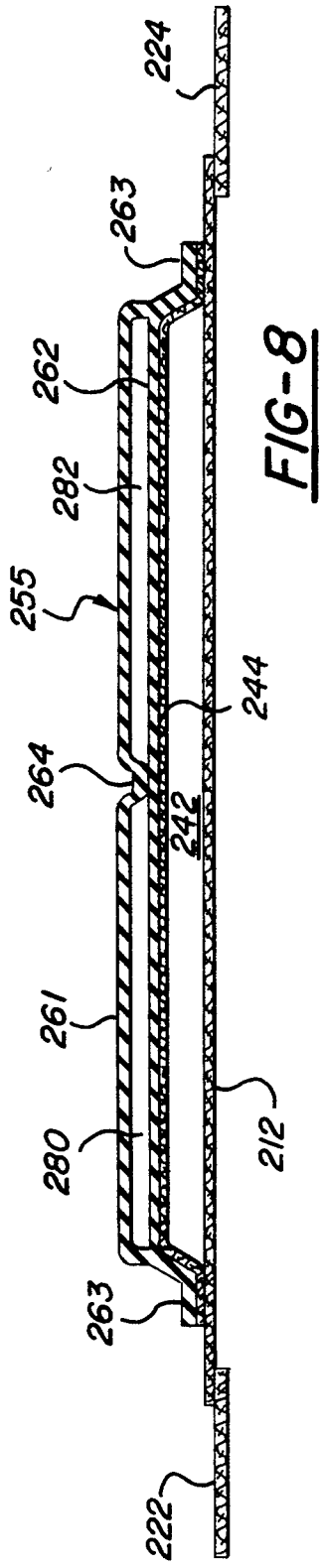

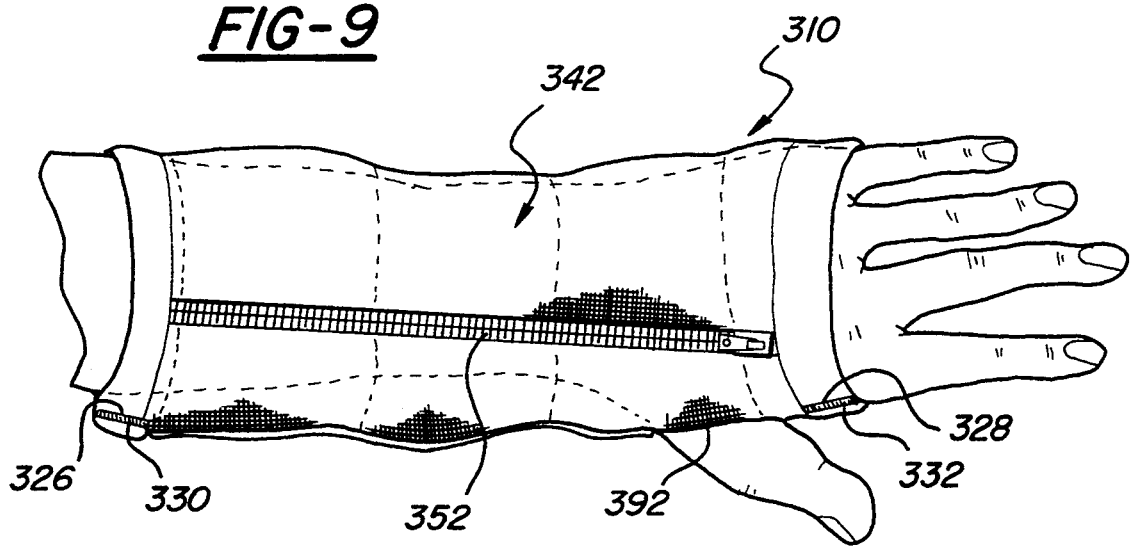
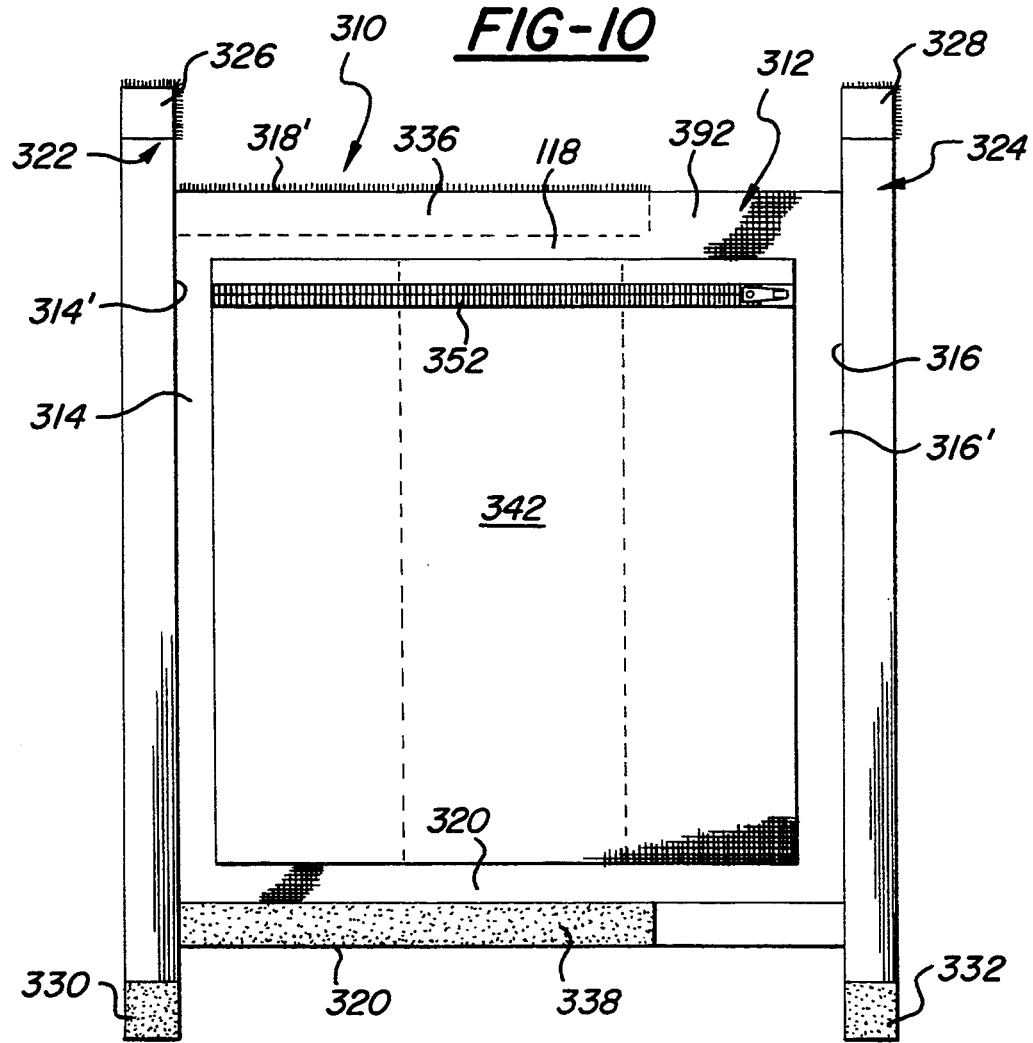

THERMAL WRAP FOR A BODY MEMBER

FIELD OF THE INVENTION

This invention relates to thermal wraps useful for applying heat or cold to a member of the body. It is useful for either therapeutic or preventive treatment.

BACKGROUND OF THE INVENTION

There is a need for a thermal wrap which will effectively apply heat or cold to a limb, joint or other body member and also permit mobility with minimal encumbrance of freedom of movement. The thermal wrap must be easy to apply with a desired tightness. Further, it must be comfortable for the user and should allow vigorous activity of the body without becoming displaced from the affected area. It should, for example, withstand athletic activity such as running and skiing and also be suitable for a sedentary user. Further, the thermal wrap should be of low cost and it should accept a thermal medium for either cold or hot treatment. The thermal wrap should also be durable and reusable and preferably it should be made of breathable material.

It is well known that the application of heat or cold provides effective therapy for muscle and joint injuries. When properly applied, a thermal wrap is effective to provide pain relief from sprains, strains, bruises, muscle trauma and other injuries to the body. For effectiveness, the thermal wrap should provide intimate engagement of the thermal medium, whether hot or cold, with the affected area to obtain optimum heat transfer. In some applications, a controlled degree of compression on the affected area is desirable for enhancing the therapeutic effect.

Thermal wraps of wide variety have been proposed in the prior art. However, none has satisfactorily met the needs for a thermal wrap in regard to therapeutic effectiveness together with ease of use and mobility, as discussed above.

The Palmacci patent U.S. Pat. No. 4,976,262 granted Dec. 11, 1990 discloses an ice bag holding device especially adapted for application to the knee. This thermal wrap holds an ice bag of special design against the affected area by wrapping it around the knee joint and uses hook and loop fasteners for holding it in a stretched condition. The wrap is constructed of a stretchable material.

The Tampa patent U.S. Pat. No. 4,628,932 granted Dec. 16, 1986 discloses a knee ice pack which is wrapped around the knee and fastened with hook and loop fasteners. Waterproof compartments for holding ice are provided with a zipper closure at the top.

The Hubbard et al. patent U.S. Pat. No. 4,688,572 granted Aug. 25, 1987 discloses a thermal pack for application to the knee. This thermal pack comprises first and second pockets for holding thermal material which are connected together by a stretchable section. The thermal pack is wrapped around the knee with the stretchable section over the knee cap and held in place by straps in the region of the pockets which are secured by hook and loop fasteners.

Other prior art devices are described in the following patents: Murphy U.S. Pat. No. 5,074,300 granted Dec. 24, 1991 for "Reusable Fabric-Covered Heat-Exchange Bag"; Laroco U.S. Pat. No. 4,899,749 granted Feb. 13, 1990 for "Thermal Vascular Dilating Device And Method"; Swearingen U.S. Pat. No. 4,805,619 granted Feb. 24, 1989 for "Therapeutic Cooling Scarf, Wrap Or Collar"; Hanson et al. U.S. Pat. No. 4,776,042 granted Oct. 11, 1988 for "Cryokenetic Headband"; Abt U.S. Pat. No. 4,641,655 granted Feb. 10, 1987 for "Therapeutic Cooling Wrap"; and Waldrum U.S. Pat. No. 2,949,914 granted Aug. 23, 1960 for "Ankle Ice Pack".

A general object of this invention is to provide an improved thermal wrap which overcomes certain disadvantages of the prior art.

SUMMARY OF THE INVENTION

This invention provides a thermal wrap which is easy to use and which allows for mobility including vigorous activity without unwanted displacement while providing effective therapy to the affected area.

In accordance with the invention, this is provided by a thermal wrap comprising a flexible pouch for containing a thermal medium with a fastener system which keeps the pouch in place over the affected area with a controlled degree of compression on the affected area. A wrap fastener is effective over the pouch bandwidth to establish the amount of compression applied to the affected area and one or more adjustable cinch bands, which engage the body member remote from the affected area, apply an adjustable amount of holding force independently of the compression applied over the pouch bandwidth.

Further, in accordance with this invention, a controlled compression may be applied to the affected area independently of the tightness of the cinch bands. This is accomplished by an air bladder overlying the thermal pouch which may be pressurized to obtain the desired degree of compression applied directly to the affected area under the pouch.

A complete understanding of this invention may be obtained from the detailed description that follows taken with the accompanying drawings.

DESCRIPTION OF THE DRAWINGS

FIG. 7 shows a third embodiment of the knee wrap with an air bladder for compression control;

FIG. 8 is a cross-sectional view taken on lines 8—8 of FIG. 7;

FIG. 9 illustrates a wrist wrap in place on a person's wrist; and

FIG. 10 shows the wrist wrap in a view of the outer surface laid flat.

BEST MODE FOR CARRYING OUT THE INVENTION

Figure 1:
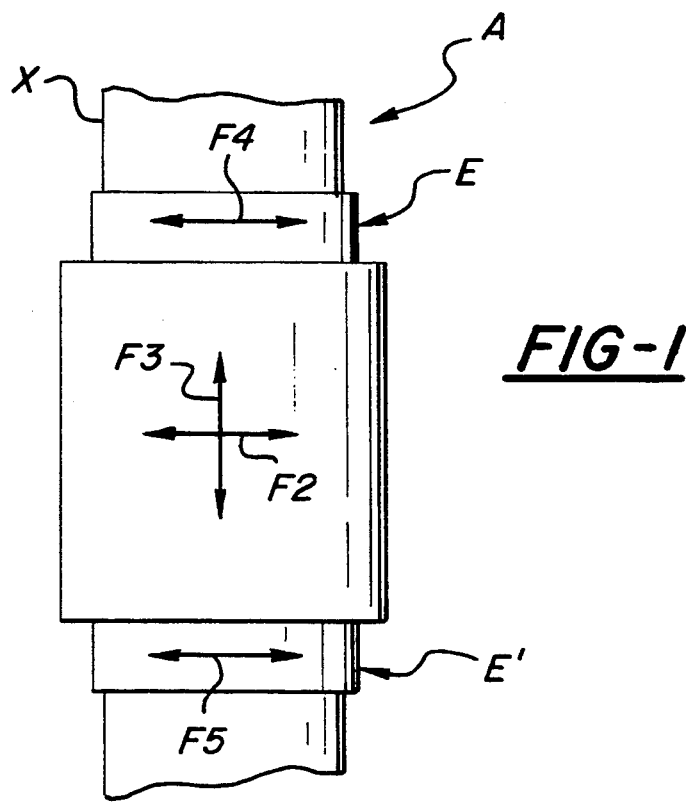
FIG. 1 is a schematic representation of the thermal wrap in a frontal view.

Referring now to the drawings, illustrative embodiments of the invention are shown in a thermal wrap for therapeutic use on a limb or joint of a person. The thermal wraps shown will be described for application to joints of the body. It will be appreciated, as the description proceeds, that the invention is adapted for a variety of applications and may be realized in other embodiments.

Before describing the structure of the thermal wrap in a specific application, the concept, principles of construction and application of the invention will be described with reference to FIGS. 1 and 2. These figures are a schematic representation of the invention and illustrate the function of the main structural parts and also illustrate the relative forces which may be obtained in use of the invention.

Figure 2:
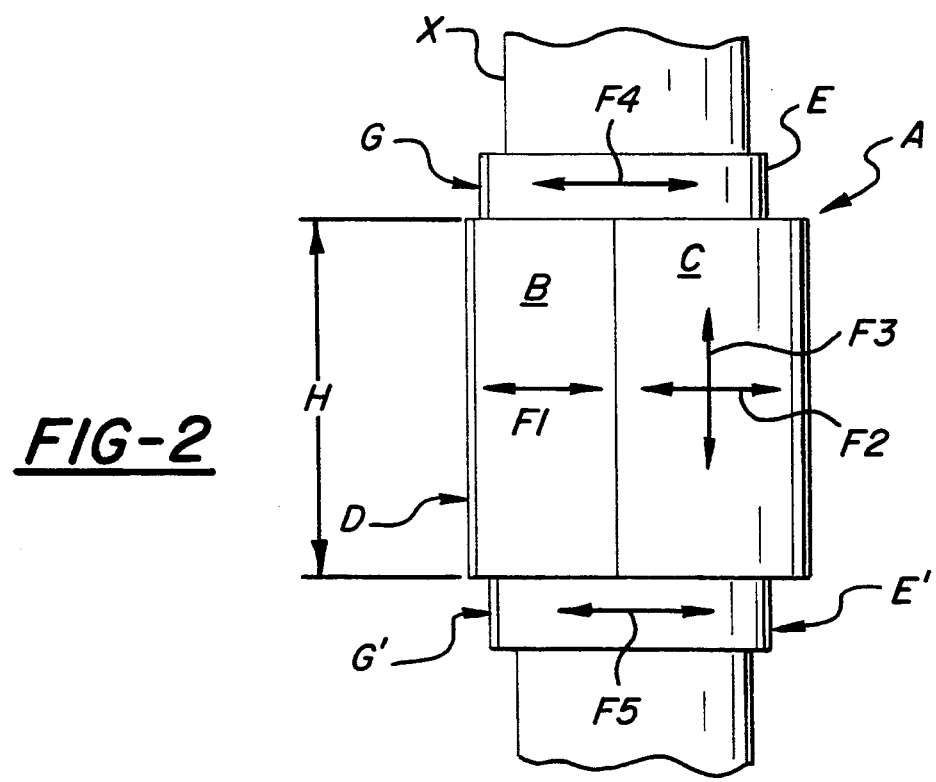
FIG. 2 is a side view of the thermal wrap of FIG. 1.

In the schematic drawings of FIGS. 1 and 2, a persons limb, e.g. leg, is represented by a cylindrical member X and is shown in front and side views. The thermal wrap A of this invention is applied to the limb by wrapping it around the limb and fastening it in place. The thermal wrap A comprises a support member B which is constructed of a generally rectangular flexible elastic sheet. A pouch C is mounted on the support member B and has inner and outer walls or panels each of which is constructed of a flexible elastic sheet. The outer panel is attached around its periphery to the support member and the underlying portion of the support member constitutes the inner panel. The pouch C is adapted to contain a thermal medium such as ice or a sealed gel package, and is provided with an opening and suitable closure for inserting and removing the thermal medium.

For application of the thermal wrap A to the limb, the support member B is wrapped around the limb in a single layer except for overlapping of the lateral edges by an amount depending upon the lateral dimensions. Preferably, the medium is inserted into the pouch C prior to wrapping. The wrap is positioned circumferentially on the limb so that the pouch C overlies the affected area to be treated. The amount of radial compression to be exerted by the wrap on the affected area of the limb is determined by the adjustment of an adjustable wrap fastener D which is engaged and tightened as desired when the wrap is applied and which is readjustable afterward. Preferably, the wrap fastener D is adapted for establishing substantially uniform tension in the support member B throughout a bandwidth H having a dimension about the same as the vertical length of the pouch C (herein called the 'pouch bandwidth').

In order to secure the thermal wrap A in place on the limb so that it remains substantially fixed despite movement of the limb, an upper anchor or cinch band E is provided and preferably, but optionally, a lower cinch band E' is provided. The cinch bands E and E' are provided, respectively, with fasteners G and G' which are individually adjustable to establish the tension in the cinch bands E and E', respectively. Each of the cinch bands E and E' may constructed of an axial extension of the support member B with a strap secured to and partially overlapping the extension. Each of the cinch bands E and E' may be provided with an elastic section which has an elasticity different from that of the remainder of the band.

The use of the thermal wrap depicted in FIGS. 1 and 2 will now be described with reference to the stresses in and the forces exerted by different parts of the wrap. A tensile stress F1 is established in the support member B and is substantially uniform in the pouch bandwidth. This tensile stress F1 is determined by the amount the support member B is stretched when the fastener D is secured. This tensile stress F1 is effective to apply a radial compressive force over the encircled portion of the limb and may be adjusted to suit the needs of the user. There is also a tensile stress F2 in the circumferential direction in the outer panel of the pouch C. The tensile stress F2 will be greater or lesser than the tensile stress F1 depending upon the elasticity of the outer panel relative to the inner panel and depending upon the amount of stretching of the outer panel due to the filling of the pouch C with a thermal medium. There will also be an axial stress F3 in the outer panel of the pouch due to the filling of the pouch. These stresses in the outer panel, especially the stress F2, and hence the radial compression applied thereby are of importance in the use of the thermal wrap because it may increase the radial compression force applied to the affected areas of the limb. If the thermal medium is granular or chunky, such as ice, a comfort factor may be involved.

As discussed above, the wrap A is held in a wrapped condition around the limb by the fastener D. The compressional force exerted by the wrap on the limb over the pouch bandwidth, may be adjusted from substantially zero to a relatively large value. This radial compression does tend to hold the thermal wrap in place but additional holding is required depending upon the expected activity of the limb. This is provided by the cinch bands E and E', at least one of which is required. If only one is used, it is preferably the upper cinch band E and, for a greater holding effect, both are preferably used. The tensile stress F4 in the cinch band E is established by the amount of stretch in the band E when the fastener G is secured. The same is true of the tensile stress F5 in the band E'. In the respective cinch bands E and E', the tensile stresses F4 and F5 are independently adjustable and determine, respectively, the radially extending compressive forces on the limb and hence, the holding force of each.

It is especially noteworthy that the compressive force applied to the affected area of the limb, i.e. under the pouch bandwidth is adjustable independently of the holding force provided by the cinch bands. Further, the compression applied under the pouch may be different from the compression applied under the remainder of the pouch bandwidth, depending upon the construction of the pouch. This independent relationship between the compression on the affected area by the pouch bandwidth and that under the cinch bands is extremely important in the use of the thermal wrap. It allows the thermal treatment of the affected area to be optimized by establishing the compression in the pouch bandwidth in accordance with the condition of the affected area. This compression may range from substantially zero to a relatively high value. At the same time, the radial compression established in the upper and lower cinch bands may be adjusted independently of the pouch bandwidth and independently of each other. This combination enables the optimum treatment of the affected area with a selected compression while permitting the holding force of the thermal wrap to be adjusted in accordance with the desired degree of activity of the limb. Thus, the effectiveness of the thermal wrap may be maximized while the mobility and the comfort of the user are also maximized.

Preferred Embodiments

In view of the foregoing discussion of the thermal wrap of this invention, several different embodiments and the details of construction will now be described setting forth the best mode now contemplated for carrying out the invention.

The Knee Wrap (First Embodiment)

Figure 3:
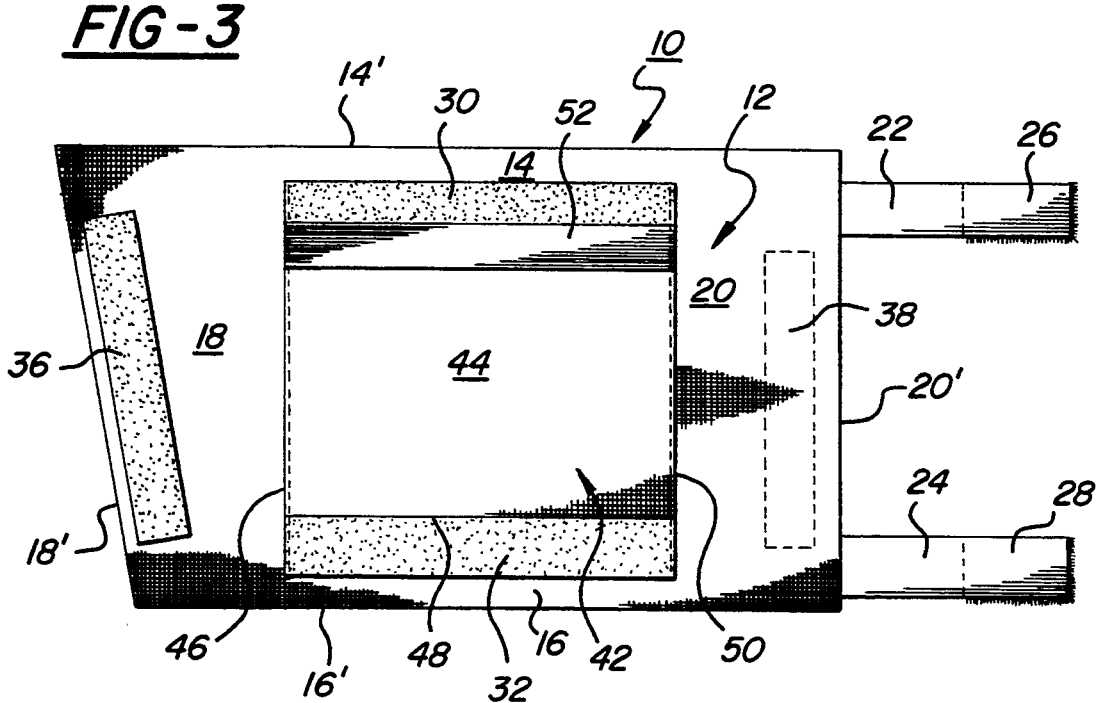
FIG. 3 is a view of the knee wrap showing the outer surface laid flat.
Figure 4:
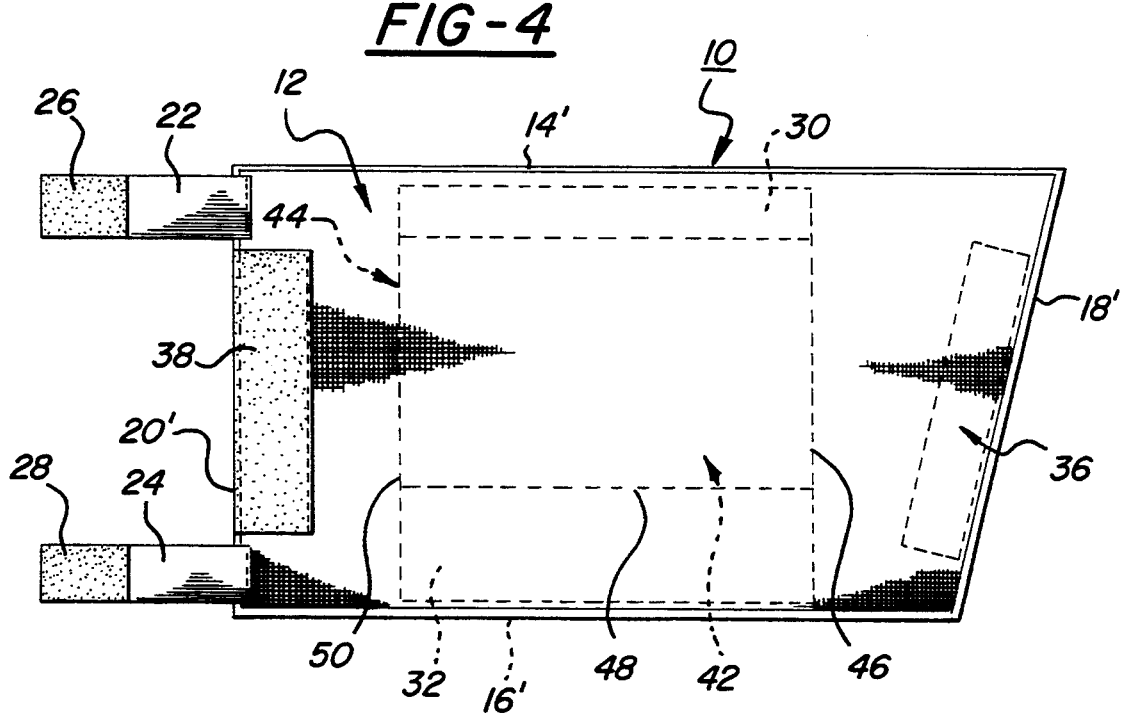
FIG. 4 shows the inner surface of the wrap of FIG. 3.
Figure 5:
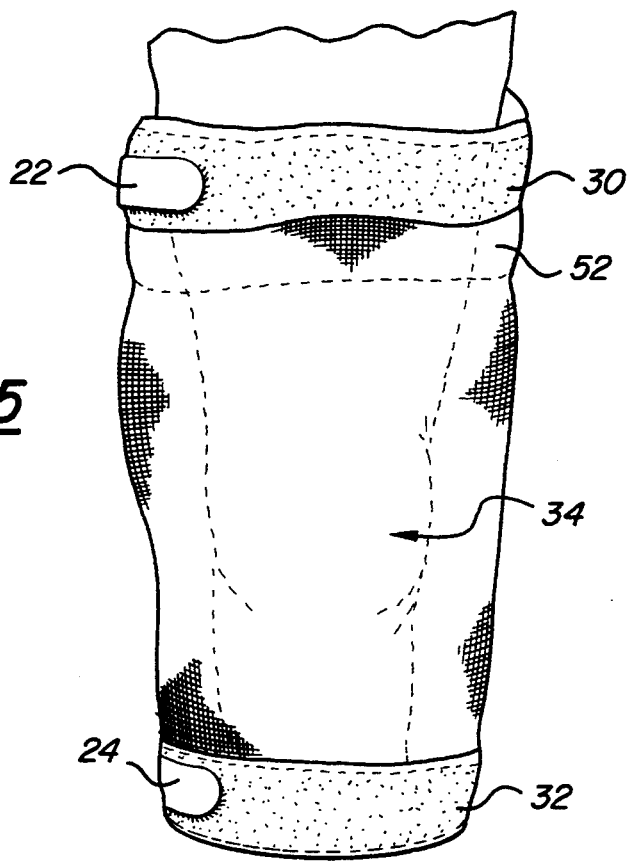
FIG. 5 shows the knee wrap in place on a person's knee.

Referring now to FIGS. 3, 4 and 5, the invention will now be described in a knee wrap application.

The knee wrap 10 comprises, in general, a support member 12 which carries a flexible pouch 42 having a pouch wall or panel 44 secured to the support member 12. The placement of the pouch panel 44 on the support member 12 provides a top border 14 between the top edge 14' and the pouch and it also provides a bottom border 16 between the bottom edge 16' and the pouch. Similarly, it provides a left side border 18 and a right side border 20 between the side edges 18' and 20', respectively. The support member 12 is provided with a compression adjustment or wrap fastener which comprises first and second coacting parts 36 and 38. It is also provided with upper and lower flexible straps 22 and 24, respectively, which form a part of the upper and lower cinch bands. Upper and lower cinch band fasteners comprise, respectively, coacting parts 22 and 36 for the upper fastener and parts 24 and 36 for the lower fastener. The wrap 10 is shown in FIG. 5 as it appears when it is applied by wrapping around a person's knee 34.

The structure of the knee wrap of FIGS. 3 through 5 will now be described in more detail. The support member 12 comprises a flexible elastic sheet of cloth which is generally rectangular in shape and suitably trapezoidal to account for the diminishing diameter of the leg area from above the knee joint to below it. The support member is dimensioned from top to bottom so as to cover the knee and from side-to-side so as to permit wrapping of a single layer around the knee joint with some overlap of the fastener parts 36-38. The cloth of the support member 12 is preferably a stretch fabric such as those sold under the names "Darlexx" TM . "Lycra" TM or "Spandex" TM which provide omnidirectional elasticity. In some applications, the cloth may be "Neoprene TM" rubber or it may be a paper-like material with a plastic coating or binder as "Tyvek" TM (a trademark of Dupont) which is made of one hundred percent high density polyethylene fillers and binders (Hdep-2). The edges 14', 16', 18' and 20' of the support member 12 are folded over upon themselves and joined to the support member 12 along a line by stitching (not shown) to form a double layer.

The flexible pouch 42 comprises the outer pouch panel 44 which is disposed in face-to-face relation with a central portion of the support member 12 and is joined thereto by stitching 46, 48 and 50. The pouch panel 44 is preferably joined, as described, to the support member 12 with both of them in an unstressed condition to form an expandable pouch which is formed by the outer panel 44 and an inner panel which comprises the facing portion of the support member 12. The pouch has an opening at the upper edge in the region between the stitching 46 and 50 for insertion and removal of the thermal medium. The panel 44 is preferably constructed of the same material as support member 12. A closure is provided for the opening to ensure containment of the thermal medium. This closure comprises a two-part fastener of the hook and loop type and comprises coacting fastener strips 30 and 52. The fastener strip 30 extends across the top of the pouch and is mounted on the support member 12 as by stitching (not shown). The fastener strip 52 is mounted on the inner side of the panel 44 and extends across the opening but is of narrower width than the strip 30. This leaves the upper portion of the fastener strip 30 exposed for a purpose which will be described below.

The wrap fastener for securing the overlapping ends of wrap together comprises a hook and loop fastener with the fastener strips 36 and 38. The fastener strip 36 is mounted on the left side border 18 substantially parallel to the left side edge 18' on the outer face of the support member 12. The coacting fastener strip 38 is mounted on the border 20 substantially parallel to the right side edge 20' and on the inner face of the support member 12.

For securing the thermal wrap in place on the limb, the upper cinch band is provided which comprises the flexible elastic strap 22 and the upper border 14 of the support member 12. The strap 22 is secured by stitching at one end to the right side border 20 in alignment with the upper border 14. Similarly, the lower cinch band comprises an flexible elastic strap 24 and the lower border 16 of the support member 12. The strap 24 is secured by stitching to the right side border 20 in alignment with the lower border 16. An adjustable fastener for the upper cinch band is provided by a hook and loop fastener comprising a fastener patch 26 and a coacting strip 30. The patch 26 is mounted by stitching on the free end of the support strap 22. Similarly, an adjustable hook and loop fastener is provided for the lower cinch band and comprises a patch 28 mounted on the free end of support strap 24 and a coacting strip 32 mounted on the exposed face of the pouch panel 44 by stitching.

The fasteners referred to above as hook and loop fasteners are of the type sold under the name "Velcro TM". It will be understood that other fasteners which provide adjustability may be used for the cinch and wrap fasteners such as strap-and-buckle fasteners, snap fasteners and tie strings and such others as will occur to those skilled in the art. Other closure fasteners for the pouch include plastic zip-lock fasteners (like foodbag closures), zippers and such other devices as will occur to those skilled in the art.

The pouch 42 is adapted to receive a thermal medium such as ice, hot water, pre-packaged gels and anti-freeze liquids. Preferably, the thermal medium is a pre-packaged gel of the type which may be heated or chilled and is flexible even when chilled.

For use with the pre-packaged thermal material, the pouch of the thermal wrap does not need to be waterproof. However, if the pouch is to be filled with ice or water, waterproof construction is required. Waterproof construction may be provided by using a waterproof material for the support member 12 such as "Darlexx" TM, rubber or "Tyvek" TM referred to above. Depending upon the materials selected for the pouch panel 44 and the support member 12, the joinder therebetween along the lines 46, 48 and 50 may be provided by known techniques such as thermal welding, laser welding, laser enhanced bonding or heat staking. For a waterproof pouch, the closure fastener may be provided by a water-tight zipper or a plastic zip lock. One example of a preferred material for a waterproof pouch uses "Darlexx" TM style 3650 (available from Darlington Fabrics Corp., New York, N.Y.) for both the support member 12 and the pouch panel 44. The seams are formed by laser enhanced bonding, a process by which a laser beam drives a polymer adhesive bonding agent into the materials being joined. This process is available from Lightseam Technologies, Inc. of Golden, Colo. Also the seams of "Darlexx" TM may be formed by liquid adhesive such as GE Primer 118 and GE Silicon 4179 available from General Electric Company of Schenectady, N.Y. Also, seams may be formed by composite tapes having a thermoplastic adhesive layer and an outer layer for abrasion resistance and appearance such as that available from Electro-Seal Corporation or Mann Industries. Such seam tapes can be applied with hot-air sealers available from Pfaff Corporation.

The Knee Wrap (Second Embodiment).

Figure 6:
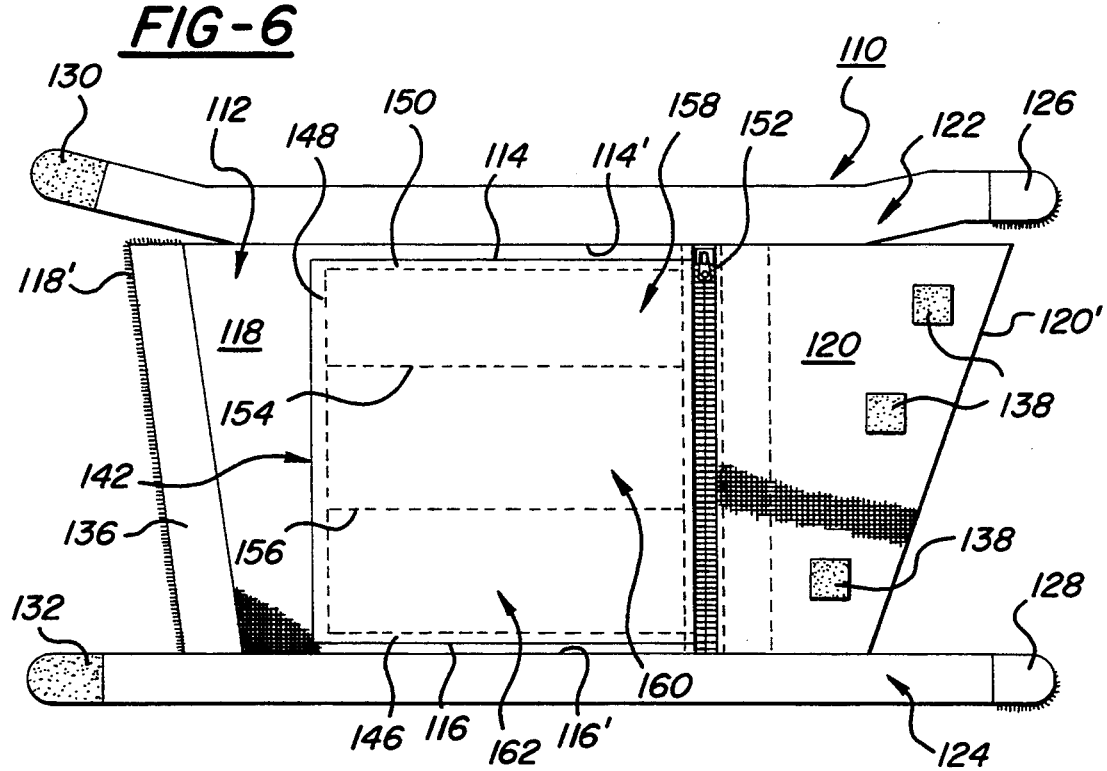
FIG. 6 shows a second embodiment of the knee wrap.

A second embodiment of the knee wrap is shown in FIG. 6 and is similar to that of FIGS. 3, 4 and 5. In the description of this embodiment, the reference numbers used in FIG. 6 for parts which correspond to parts in FIGS. 3, 4 and 5, are greater by one hundred than the numbers in FIGS. 3, 4 and 5.

Referring now to FIG. 6, the construction of the support member 112 is similar to support member 12 of the first embodiment and differs in that the upper and lower borders 114 and 116 are relatively narrower and the upper and lower cinch bands comprise separate straps 122 and 124. The straps are joined to the support member 112 by stitching and are constructed of a less easily stretched material (i.e. having a higher stretch modulus of elasticity) than material of the support member. The strap 122 is provided with a hook and loop fastener comprising a patch 126 mounted on one end of the strap and a coacting patch on the other end. Similarly, the strap 124 is provided with a fastener comprising a patch 128 mounted on one end and a coacting patch 132 mounted on the other end.

The pouch panel 144 is of the same construction as the pouch panel 44 of the first embodiment except that the opening is provided on the side of the pouch 142 and the closure fastener comprises a zipper 152. A further difference is that the pouch 142 is divided into plural compartments 158, 160 and 162 by a pair of joinder lines connecting the panel 144 to the support member 120 which are provided by stitching 154 and 156. This arrangement is especially useful for a thermal medium of flowable constituency such as granular, gel or liquid material to ensure an even distribution thereof over the affected area.

The second embodiment, as shown in FIG. 6, is provided with a wrap fastener similar to that of the first embodiment. It differs in that discrete fastener patches 138 (instead of a continuous strip 38) are mounted on the right hand border 120 for coacting with the velcro strip 136 on the left hand border 118.

The second embodiment, may have a non-waterproof pouch or a waterproof pouch by selection of the appropriate materials and parts as discussed above.

The Knee Wrap (Third Embodiment)

A third embodiment of the invention in a knee wrap is shown in FIGS. 7 and 8. This embodiment is like the second embodiment except that a pressurized air bladder is added for adjustment of the radial compression applied to the affected area. In this embodiment, those parts which correspond to similar parts in the second embodiment are referred to by the same reference numbers except that the first digit is "2" instead of "1". The construction of the support member 212, the thermal medium pouch 242 and the fasteners are the same as in the second embodiment. The difference is that the air bladder 255 is superimposed on the pouch 242.

The air bladder 255 comprises a thin airtight flexible elastic bladder joined around its periphery to the panel 244 to provide an airtight enclosure. Preferably, the bladder material has a much higher stretch modulus than panel 244. The bladder 255 has outer and inner walls 261 and 262 which are joined at their peripheral edges to form a flange 263. It is suitably constructed of rubber and the seams may be formed by vulcanizing. The flange which encircles the bladder serves for securement to the panel 244 and support member 212. For this purpose, the flange 263 is joined by stitching 246 and 250 along its upper and lower edges, respectively, to the panel 244 and the support member 212; is joined by stitching 266 and 268, along its sides to the panel 244 and support member 212. Additionally, the walls 261 and 262 of the bladder are joined together by a joint 264 which provides side-by-side bladder compartments 280 and 282. The joint 264 has one end 276 spaced from the end of the bladder to provide an air passage between the compartments 280 and 282. The joint 264 restricts the bulging of the panel 262 and the deformation of the panel 244 which might otherwise occur. The joint 264 also facilitates bending of the wrap along the line of the joint and minimizes interference with the flexing of the knee being treated.

In order to pressurize the air bladder 255, an air pump 272 is built into the air bladder 255, as shown in the lower left hand corner of the air bladder. The pump 272 is manually actuated by a finger or thumb to pump air into the bladder and is manually actuated to release pressure as desired. The pump 272 is like that used in the high top basketball shoes sold by Reebok and known as "THE PUMP" TM. Obviously, a pump which is separate and detachable from the thermal wrap may be used if desired. Such a pump, with a suitable valve in the bladder, may be like those used for inflating basketballs and footballs.

When the air bladder 255 is not pressurized, the thermal wrap 210 functions in the same manner as the thermal wrap 110. When the air bladder 255 is pressurized, the wrap fastener, comprising fastener parts 236 and 238, is tightened and the air bladder expands against the pouch 242 and increases the compressive force applied to the limb.

The Wrist Wrap

An embodiment of the invention for use as a thermal wrap for a wrist is shown in FIGS. 9 and 10. It is similar to the second embodiment of the knee wrap shown in FIG. 6. In FIGS. 9 and 10, those parts which correspond to similar parts in FIG. 6 are referred to by the same reference numbers except that the first digit is "3" instead of "1".

Referring now to FIGS. 9 and 10, the construction of the support member 312 is similar to support member 112 of FIG. 6 except that it is rectangular instead of trapezoidal.

The pouch 342, the cinch bands comprising straps 322 and 324, and the cinch band fastener parts 326–330 and 328–332 are the same as FIG. 6.

The wrap fastener is similar to that of FIG. 6 except that the hook and loop fastener strips 336 and 338 do not extend the full width of the pouch 342 thereby leaving an opening in the wrap for the thumb of the user.

As illustrated in FIG. 9, the wrist wrap is applied to the wrist by wrapping it around the lower arm and wrist with the thumb extending through the opening 392 and engaging the wrap fastener parts 336 and 338. Then, the lower strap 324 is pulled to the desired tightness around the hand and the cinch band fastener parts 328–332 are engaged. Finally, the cinch band comprising strap 322 is tightened as desired around the arm and the cinch band fastener parts 326 and 330 are engaged.

Conclusion

A thermal wrap has been described which can be realized in various embodiments and which is useful for many applications. It embodies new structural arrangements and principles of operation which provide great improvement over the prior art thermal wraps.

Although the description of this invention has been given with reference to a particular embodiment, it is not to be construed in a limiting sense. Many variations and modifications of the invention will now occur to those skilled in the art. For a definition of the invention, reference is made to the appended claims.

What is claimed is:

1. A thermal wrap for application to a body member, comprising:
    a flexible pouch having edges extending thereabout,
    a flexible border surrounding said pouch and connected to the edges of said pouch,
    a wrap fastener having a first part secured to said border on a lateral side of the pouch and having a second part secured to said border on an opposite lateral side of the pouch,
    said border having a stretchable portion between said pouch and at least one of the wrap fastener parts,
    a first cinch strap secured to said border above said pouch and a second cinch strap secured to said border below said pouch,
    a first cinch fastener having a first part thereof secured to said border above said pouch and having a second part secured to said first cinch strap,
    a second cinch fastener having a first part secured to said border below said pouch and having a second part secured to said second cinch strap, and
    said border having a stretchable portion between said wrap fastener and said first and second cinch straps and fasteners whereby said wrap fastener and said first and second cinch straps and fasteners are adapted to secure the thermal wrap to said body member with substantially mutually independent adjustable tension forces.

2. A thermal wrap as defined in claim 1 wherein said pouch comprises inner and outer panels constructed of elastic material.

3. A thermal wrap as defined in claim 2 wherein said elastic material has omnidirectional elasticity.

4. A thermal wrap as defined in claim 2 wherein said border has first and second side border portions on opposite sides of the pouch and has upper and lower border portions disposed above and below the pouch, respectively, said side border portions being made of the same material as one of the panels of said pouch.

5. A thermal wrap as defined in claim 4 wherein all of said border portions are constructed of the same material as one panel of said pouch and being formed as an extension thereof.

6. A thermal wrap as defined in claim 5 wherein said inner and outer panels of said pouch are made of the same material.

7. A thermal wrap as defined in claim 1 wherein an inflatable bladder is secured to said border and is adapted to coact with said pouch to tighten said thermal wrap on said body member and urge said pouch against said body member.

8. A thermal wrap as defined in claim 1 wherein said border has a stretchable portion between said pouch and both of said wrap fastener parts.

9. A thermal wrap for application to a body member, comprising:
    a flexible stretchable cloth member including inner and outer layers secured together to form a pouch having an opening for receiving a thermal medium in the pouch,
    said cloth member having first and second parts,
    a wrap fastener having parts mounted on said cloth member for connecting said first part of said cloth member to said second part after said cloth member has been wrapped around said body member whereby said pouch is adapted to be held against said body member with an adjustable tension force in said wrap fastener,
    and first and second cinch straps secured to said cloth member on portions of said cloth member located above and below said pouch, respectively, for wrapping around said body member above and below said pouch, each of said straps including a cinch fastener for securing it wrapped around said body member whereby said cloth member is adapted to be held against said body member with an adjustable tension force in said first cinch strap and cinch fastener and in said second cinch strap and cinch fastener, and
    said cloth member having a stretchable portion between said pouch and said wrap fastener and also between said wrap fastener and said first and second cinch straps and cinch fasteners whereby said wrap fastener and said first and second cinch straps and fasteners are adapted to secure the thermal wrap to said body member with substantially mutually independent adjustable tension forces.

10. A thermal wrap as defined in claim 9 wherein said cloth member is stretchable omnidirectionally.

11. A thermal wrap as defined in claim 9 including a closure for said opening.

12. A thermal wrap as defined in claim 9 wherein said cinch straps are stretchable.

13. A thermal wrap as defined in claim 9 wherein said cloth member comprises first and second sheets of cloth forming said inner and outer layers, respectively, said wrap fastener parts being mounted on said first sheet for holding said first sheet in contact with said body member whereby said second sheet can be stretched independently of said first sheet of cloth.

14. A thermal wrap as defined in claim 13 wherein each of said cinch straps is secured to said first sheet of cloth exclusively of said second sheet of cloth.

15. A thermal wrap as defined in claim 9 wherein an inflatable bladder is mounted on said pouch and operates on inflation to urge said pouch toward said body member.

16. A thermal wrap as defined in claim 15 wherein said bladder is superimposed on said pouch.

17. A thermal wrap as defined in claim 15 wherein said bladder has a stretch modulus significantly greater than said cloth member.

18. A thermal wrap as defined in claim 15 wherein a joint separates said bladder into connected compartments and restricts deformation of said outer layer of said pouch.

19. A thermal wrap as defined in claim 15 wherein a joint separates said bladder into connected compartments and restricts bulging of said bladder and deformation of said outer layer of said pouch.

* * * * *